United States Patent [19]

O'Lenick, Jr.

[11] Patent Number: 5,444,154
[45] Date of Patent: Aug. 22, 1995

[54] CROSSLINKED PROTEIN POLYMERS AS HUMECTANTS

[75] Inventor: Anthony J. O'Lenick, Jr., Lilburn, Ga.

[73] Assignee: Siltech Inc., Norcross, Ga.

[21] Appl. No.: 260,737

[22] Filed: Jun. 15, 1994

Related U.S. Application Data

[60] Continuation-in-part of Ser. No. 183,754, Jan. 24, 1994, Pat. No. 5,350,858, which is a division of Ser. No. 901,200, Jun. 19, 1992, Pat. No. 5,298,656, which is a continuation-in-part of Ser. No. 813,449, Dec. 26, 1991, Pat. No. 5,153,294.

[51] Int. Cl.⁶ .................... C07K 3/00; C07D 403/12; A61K 7/06
[52] U.S. Cl. .................... 530/356; 530/357; 530/372; 530/375; 530/378; 530/406; 530/410; 530/815; 530/816; 424/70.14; 525/54.1; 548/313.7; 554/52; 564/224
[58] Field of Search ............ 530/356, 357, 372, 375, 530/398, 406, 410, 815, 816; 424/70, 71; 525/54.1; 548/313.7; 554/52; 564/224

[56] References Cited

U.S. PATENT DOCUMENTS

| | | | |
|---|---|---|---|
| 4,209,449 | 6/1980 | Mayhew et al. | 548/313.7 |
| 4,800,077 | 1/1989 | O'Lenick, Jr. et al. | 424/90 |
| 5,070,171 | 12/1991 | O'Lenick, Jr. | 528/33 |
| 5,100,956 | 3/1992 | O'Lenick, Jr. | 525/54.1 |
| 5,210,133 | 5/1993 | O'Lenick, Jr. | 525/54.1 |
| 5,243,028 | 9/1993 | O'Lenick, Jr. | 530/375 |
| 5,271,926 | 12/1993 | Kure et al. | 424/71 |
| 5,274,101 | 12/1993 | O'Lenick, Jr. | 548/112 |
| 5,280,099 | 1/1994 | Imperante et al. | 528/28 |

*Primary Examiner*—William H. Beisner
*Assistant Examiner*—Abdel A. Mohamed

[57] ABSTRACT

The present invention relates to a series of novel crosslinked polymers. The compounds of the present invention are prepared by the reaction of chloracetic acid with a pendant hydroxyl group which is present on a polyoxyalkylene polymer, followed by the reaction of the halo-ester with a protein or amino acid to give a crosslinked protein compound. In a preferred embodiment the polyoxyalkylene glycol has been prepared by the reaction of both ethylene oxide and propylene oxide. In a more preferred embodiment, the ethylene oxide is at the terminal portion of the molecule and the propylene oxide is in the center. The proteins of the present invention plate out on the surface of hair skin and once dry act as humectants, trapping moisture to the hair. This results in hair which is fuller, has less static and is cosmetically more appealing. This combination of properties makes these polymers ideally suited for use in personal care applications.

16 Claims, No Drawings

CROSSLINKED PROTEIN POLYMERS AS HUMECTANTS

RELATED APPLICATIONS

This application is a continuation in part application of Ser. No. 08/183,754, filed Jan. 24, 1994, now U.S. Pat. No. 5,350,858, which is in turn a divisional application of Ser. No. 901,200 filed Jun. 19, 1992 which is now U.S. Pat. No. 5,298,656, which is a continuation in part of Ser. No. 813,449 filed Dec. 26, 1991, now U.S. Pat. No. 5,153,294.

BACKGROUND OF THE INVENTION (1) Field of Invention

The present invention relates to a series of novel quaternary protein polymers and an intermediate useful in their preparation. Since the compounds of the present invention are high molecular weight, they have a high degree of oxidative stability, even at elevated temperatures. The proteins of the present invention plate out on the surface of hair skin and once dry act as humectants, trapping moisture to the hair. This results in hair which is fuller, has less static and is cosmetically more appealing. These combination of properties makes these polymers ideally suited for use in personal care applications. The crosslinked proteins of the present invention are highly substantive to keratinous materials like hair and skin and promote absorption and retention of water.

The compounds of the present invention are prepared by the reaction of chloracetic acid with a pendant hydroxyl group which is present on a polyoxyalkylene polymer, followed by the reaction of the halo-ester with the amino group in a protein. In a preferred embodiment the polyoxyalkyiene glycol has been prepared by the reaction of both ethylene oxide and propylene oxide. In a more preferred embodiment, the ethylene oxide is at the terminal portion of the molecule and the propylene oxide is in th center. This results in the best combination of solubility and highest percentage reacted.

(2) Object of the Invention

It is the object of the present invention to provide a series of novel polymeric quaternary protein compounds which unlike the silicone containing proteins of the prior art, plate out on the surface of hair skin and once dry act as humectants, trapping moisture to the hair. This results in hair which is fuller, has less static and is cosmetically more appealing. The compounds of the present invention are linked through the nitrogen portion of the amino acid or protein. Incorporation of this type of group into the molecule results in increased solubility in many organic solvents. The compounds also contain varying amounts of ethylene oxide and propylene oxide in the molecule. This results in the ability to vary water solubility, foaming tendencies and introduce an inverse cloud point into the molecule.

Still another object of the present invention is to provide a series of quaternary polymers which have differing solubilities in water and organic solvents. This is achieved by selection of the raw materials chosen.

Application of the compounds of the invention can be from solvent, aqueous dispersion or solution, or applied neat in these process. It is anticipated that the effective conditioning concentration of the compound of this invention ranges from 0.1% to 25% by weight.

The polyoxyalkylene glycol polymers, suitable as raw materials, in a preferred embodiment, contain varying amounts of ethylene oxide, propylene oxide or mixtures thereof. The presence of a mixed polyoxyethylene/polyoxypropylene glycol in correct location within in the molecule, results in liquidity, low foam, solubility and enhanced reactivity. It also results in compounds with an inverse cloud point. Inverse cloud point phenomenon are well known to those skilled in the art of nonionic surface active agents. The inverse cloud point is defined as a temperature above which the polymer has minimal solubility in water. If heat is applied to an aqueous solution of the nonionic at the inverse cloud point the material will become insoluble, and the solution will turn milky. It is at this point that the polymer has minimal water solubility. Since the product is no longer in solution at above this temperature, it is within this temperature range that the product has maximum substantivity to a fiber. The ability to use temperature to deposit a lubricant, antistat onto a fiber offers a great advantage in cost effectiveness of fiber treatment, and results in less product usage.

(3) Description of the Arts and Practices

U.S. Pat. No. 5,100,956 to O'Lenick, Jr. discloses silicone derivitized proteins. The product is a phosphate containing silicone protein. U.S. Pat. No. 5,223,048 to O'Lenick, Jr. discloses phosphate free silicone containing protein polymers. These protein molecules contain silicone which provides a flexible film on the hair or skin which are hydrophobic, that is they make the hair less permeable to water. While this results in the ability to maintain the shape of hair like for example a curl, the hair respells rather than attracts water. Specifically, the silicone proteins act as styling aides.

The compounds of the present act oppositely to the silicone protein derivatives, in that they promote water absorption and moisturization of the hair shaft. This is particularly important for hair which has been permed, straightened or otherwise processed. Processed hair becomes dry, brittle and straw like. The incorporation of a humectant protein polymer onto this treated hair results in an immediate palliative affect and a longer term reconstructive affect upon the hair. These affects are surprising and unexpected.

THE INVENTION

1) SUMMARY OF THE INVENTION

Proteins are materials which play a critical role in all biological processes. They are natural products and have enjoyed increasing use in personal care products as conditioners, humectants and softeners. Natural proteins, which are high molecular weight polymers, are generally hydrolyzed into lower molecular weight proteins to obtain water solubility. The water solubility results in easier formulating, but the soluble proteins are less substantive to hair and skin. Consequently, the water soluble proteins end up washed off the substrate being treated. The compounds of the present invention are far more substantive since they have been crosslinked through a difunctional polyoxyalkylene glycol linking group. Not only does this result in more substantive to the skin and hair, the presence of alkylene oxide in the silicone polymer in a preferred embodiment results in a protein with an inverse cloud point. The crosslinked protein forms an insoluble matrix above this temperature which deposits on the hair and skin. This suggests the use of these materials in treatment products were heat is applied, like hot oil treatments.

Amino acids are the basic structural units of proteins. An amino acid has both an amino group and a carboxyl group.

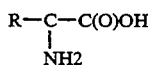

The amino acids are well known to those skilled in the art. They are: Alanine, Arginine, Asparagine, Aspartic Acid, Glutamine, Glycine, Histidine, Isoleucine, Leucine, Lysine, Methonine, Phenylalanine, Proline, Serine, Threonine, Tryptophan, Tyrosine, Valine. Amino acids are one of the "amino acid source compounds" selected frm the group consisting of a protein and amino acid, which can be used in the practicce of the present invention.

In proteins the carboxyl group of one amino acid is joined to the carboxyl group of another amino acid in an amide bond. When this aide bond is in a protein it is called a peptide bond. Many amino acids are joined in peptide bonds to form a polypeptide chain. This polypeptide chain is what we commonly call a protein. The polypeptide has a free amino group and a free carboxyl group present.

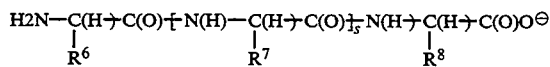

| Amino Terminal Amino Acid | Polypeptide Bonded Amino Adid(s) | Carboxy Terminal Amino Acid | s is an integer from 7 to 5,000, giving the protein a molecular weight of between 1,000 EMWU and 500,000 EMWU (EMWU is equivalent molecular weight units). Proteins, which are polymerized amino acids are another of the "amino acid source compounds" selected frm the group consisting of a protein and amino acid, which can be used in the practicce of the present invention.

The compounds of the present invention are dependant upon the reaction of the terminal amino group in either the protein or the amino acid to react with a reactive polyoxyalkylene halo ester intermediate which results in crosslinking two amino groups.

It will be clearly understood that the polypeptide bonded amino acids can be any combination of the amino acids listed above in any order. The term protein as used herein relates to two or more amino acids joined in a peptide bond.

The compounds of this invention are prepared by the reaction of a polyoxyalkylene glycol polymer conforming to the following structure:

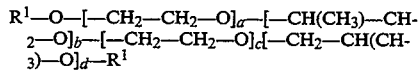

wherein;

$R^1$ is —C(O)—CH$_2$—Cl a, b c and d are independently integers from 0 to 100, with the proviso that a+b+c+d be greater than 2. with amino acid source compound selected frm the group consisting of a protein and amino acid.

The reaction is typically carried out in aqueous solution at a concentration of between 20 and 80% with a preferred range of 20-40% and at a temperature of between 40 and 100 C., with a preferred temperature range of between 60 and 90 C.

PREFERRED EMBODIMENT

In one embodiment the protein is of non-animal source such as wheat, soya or vegetable.

The intermediate polyoxyalkylene glycol halo-ester is prepared as follows:

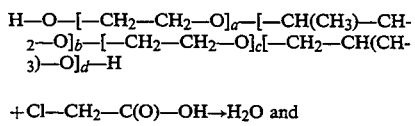

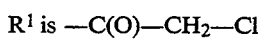

wherein

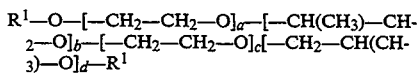

$R^1$ is —C(O)—CH$_2$—Cl

The compounds of the present invention conform to the following structure;

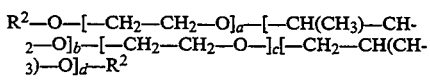

wherein;

$R^2$ is —C(O)—CH$_2$—R$^{10}$ a, b c and d are independently integers from 0 to 100, with the proviso that a+b+c+d be greater than 2;

$R^{10}$ is derived from an amino acid or protein.

RAW MATERIAL EXAMPLES

Polyoxyalkylene Glycol Compounds

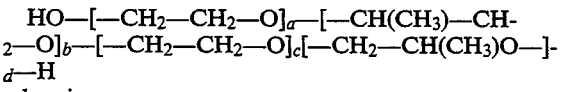

wherein;

a, b c and d are independently integers from 0 to 100, with the proviso that a+b+c+d be greater than 2.

Class 1 Polyoxethylene Glycols (b,c, and d are all 0.)

The following examples are presented with the values of a and as determined by analysis. Since products covered by trade name can change, the structure rather than the trade name is considered more important as an example.

| Example | Trade Name | Molecular Weight | a |
|---|---|---|---|
| 1 | PHENOXIDE E-200 | 200 | 4 |
| 2 | PHENOXIDE E-300 | 300 | 6 |
| 3 | PHENOXIDE E-400 | 400 | 8 |
| 4 | PHENOXIDE E-600 | 600 | 12 |
| 5 | PHENOXIDE E-900 | 900 | 20 |
| 6 | PHENOXIDE E-1000 | 1,000 | 22 |
| 7 | PHENOXIDE E-1450 | 1,450 | 32 |
| 8 | PHENOXIDE E-3350 | 3,350 | 74 |
| 9 | PHENOXIDE E-4600 | 4,600 | 104 |
| 10 | PHENOXIDE E-8000 | 8,000 | 180 |

PHENOXIDE is a registered trademark of Phoenix Chemical Inc.

Class 2

The following examples are presented with the values of a, b and c as determined by analysis. Since products covered by trade name can change, the structure, rather than the trade name is considered more important as an example.

| Example | Trade Name | a | b | c |
|---|---|---|---|---|
| 11 | PHOENIX L-31 | 1.0 | 2.1 | 1.0 |
| 12 | PHOENIX L-35 | 5.0 | 10.0 | 5.0 |
| 13 | PHOENIX L-42 | 2.5 | 5.0 | 2.5 |
| 14 | PHOENIX L-43 | 3.0 | 8.0 | 3.0 |
| 15 | PHOENIX L-44 | 6.0 | 11.0 | 6.0 |
| 16 | PHOENIX L-61 | 2.0 | 4.0 | 2.0 |
| 17 | PHOENIX L-62 | 4.0 | 8.0 | 4.0 |
| 18 | PHOENIX L-63 | 6.0 | 12.0 | 6.0 |
| 19 | PHOENIX L-64 | 8.0 | 16.0 | 8.0 |
| 20 | PHOENIX L-72 | 5.0 | 9.5 | 5.0 |
| 21 | PHOENIX L-81 | 3.0 | 5.0 | 3.0 |
| 22 | PHOENIX L-92 | 6.0 | 12.5 | 6.0 |
| 23 | PHOENIX L-101 | 4.0 | 7.5 | 4.0 |
| 24 | PHOENIX L-121 | 4.5 | 9.0 | 4.5 |
| 25 | PHOENIX L-122 | 9.0 | 18.0 | 9.0 |

PHOENIX is a registered trademark of Phoenix Chemical

Class 3 Polyoxypropylene Compounds (a, c and d are each 0)

a, c and d are all zero.

| Example | Trade Name | Molecular Weight | b |
|---|---|---|---|
| 26 | ALKAPOL PPG 425 | 425 | 7 |
| 27 | ALKAPOL PPG 600 | 600 | 10 |
| 28 | ALKAPOL PPG 1000 | 1000 | 17 |

ALKAPOL is a registered trade mark of Alkaril Chemicals Inc.

Class 4

The following examples are presented with the values of b, c and d as determined by analysis.

| Example | Trade Name | b | c | d |
|---|---|---|---|---|
| 29 | PHOENIX R 4 | 1.0 | 2.1 | 1.0 |
| 30 | PHOENIX R 20 | 5.0 | 10.0 | 5.0 |
| 31 | PHOENIX R 10 | 2.5 | 5.0 | 2.5 |
| 32 | PHOENIX R 16 | 4.0 | 8.0 | 4.0 |
| 33 | PHOENIX R 22 | 6.0 | 11.0 | 6.0 |
| 34 | PHOENIX R 8 | 2.0 | 4.0 | 2.0 |
| 35 | PHOENIX R 14 | 3.0 | 8.0 | 3.0 |
| 36 | PHOENIX R 2 | 6.0 | 12.0 | 6.0 |
| 37 | PHOENIX R 32 | 8.0 | 16.0 | 8.0 |
| 38 | PHOENIX R 19 | 5.0 | 9.0 | 5.0 |
| 39 | PHOENIX R 11 | 3.0 | 5.0 | 3.0 |
| 40 | PHOENIX R 24 | 6.0 | 12.5 | 6.0 |
| 41 | PHOENIX R 15 | 4.0 | 7.5 | 4.0 |
| 42 | PHOENIX R 18 | 4.5 | 9.0 | 4.5 |
| 43 | PHOENIX R 36 | 9.0 | 18.0 | 9.0 |
| 44 | PHOENIX R 101 | 10.0 | 10.0 | 10.0 |

Preparation of the Polyoxyalkyleneglycol Halo Ester Reaction Sequence

HO—R—OH + HO—C(O)—CH$_2$Cl→Cl—CH$_2$—OC(O)—R—C(O)CH$_2$—Cl

R is the polyoxyalkylene moiety.

The following examples further illustrate the objects and advantages of this invention, though it should be understood that the various reactants and amounts thereof, reaction conditions, and other details are merely illustrative and should not be construed to unduly limit this invention.

General Procedure

Place the indicated amount of the polyoxyalkylene glycol shown in a suitable vessel is added the desired amount of catalyst as shown under good agitation and a nitrogen sparge. Then 95.0 grams of monochloroacetic acid is added. A molar excess of 0.1 to 0.5 of chloracetic acid is added. The temperature is held between 160–200 degrees C. for two to six hours. Reaction progress is monitored by acid value analysis and at the end of the reaction reaches theoretical for the mole ratio used.

| Example | Example Number | Grams |
|---|---|---|
| 45 | 1 | 100 |
| 46 | 2 | 150 |
| 47 | 3 | 200 |
| 48 | 4 | 300 |
| 49 | 5 | 450 |
| 50 | 6 | 500 |
| 51 | 7 | 725 |
| 52 | 8 | 1,675 |
| 53 | 9 | 2,300 |
| 54 | 10 | 4,000 |
| 55 | 5 | 900 |
| 56 | 11 | 106 |
| 57 | 12 | 515 |
| 58 | 13 | 258 |
| 59 | 14 | 368 |
| 60 | 15 | 589 |
| 61 | 16 | 206 |
| 62 | 17 | 412 |
| 63 | 18 | 618 |
| 64 | 19 | 824 |
| 65 | 20 | 501 |
| 66 | 21 | 280 |
| 67 | 22 | 632 |
| 68 | 23 | 441 |
| 69 | 24 | 463 |
| 70 | 25 | 927 |
| 71 | 26 | 213 |
| 72 | 27 | 300 |
| 73 | 28 | 500 |
| 74 | 29 | 105 |
| 75 | 30 | 515 |
| 76 | 31 | 258 |
| 77 | 32 | 412 |
| 78 | 33 | 596 |
| 79 | 34 | 206 |
| 80 | 35 | 353 |
| 81 | 36 | 618 |
| 82 | 37 | 824 |
| 83 | 38 | 493 |
| 84 | 39 | 287 |
| 85 | 40 | 629 |
| 86 | 41 | 401 |
| 87 | 42 | 463 |
| 88 | 43 | 927 |

Raw Material Proteins

Proteins useful in the preparation of the products of the present invention are derived from many sources. Many are prepared by the hydrolysis of native proteins. The hydrolysis results in cleavage of some of the polypeptide bonds and increases water solubility. The hydrolysis processes are either acid, alkaline or enzymatic and are well known to those skilled in the art.

Soya Protein (CAS number 68153-28-6); Milk Protein (CAS number 9000-71-9); Wheat Protein; Oat Protein; Vegetable Protein; Keratin Protein (CAS Number 68238-35-7); Placental Protein and Collagen are all sources from which protein is derived.

The proteins useful in the preparation of the compounds of the present invention, in a preferred embodiment range in molecular weight from 1,000 equivalent molecular weight units to 500,000 equivalent molecular weight units. The equivalent molecular weight units are determined by calculation of the free amino groups. An analysis called the "amine value" is run using a standardized acid titrant. The titrations are well known to the fatty chemist and are determined as follows;

$$\text{Amine Value} = \frac{(56.1)(\text{normality})(\text{ml titrated to pH 5.5})}{(\text{weight in grams of sample})}$$

The amine value is expressed in mg KOH/gm. The amine value is then converted into equivalent molecular weight using the following formula;

$$\text{Equivalent Molecular Weight} = \frac{56,110}{\text{Amine Value (mg KOH/gm)}}$$

| Example Number | Commercial Name | Equivalent Weight |
|---|---|---|
| Protein Example A | PEPTIN 2,000 | 2,054 EMWU |
| Protein Example B | PEPTIN 5,000 | 5,010 EMWU |
| Protein Example C | POLYPRO 15,000 | 14,980 EMWU |
| Protein Example D | PEPTIN AH | 1,500 EMWU |
| Protein Example E | SOLLAGEN | 275,000 EMWU |
| Protein Example F | Wheat Protein (Hydrolyzed) | 500 EMWU |
| Protein Example G | Wheat Protein | 2,505 EMWU |
| Protein Example H | Oat Protein | 5,560 EMWU |
| Protein Example I | Oat Protein (Hydrolyzed) | 1,000 EMWU |
| Protein Example J | Soya Protein | 15,625 EMWU |
| Protein Example K | Collagen | 500,120 EMWU |
| Protein Example L | Collagen (Hydrolyzed) | 5,250 EMWU |
| Protein Example M | Keratin | 125,750 EMWU |
| Protein Example N | Keratin (Hydrolyzed) | 5,160 EMWU |
| Protein Example O | Placental Protein | 50,450 EMWU |

(PEPTIN, POLYPRO, and SOLLAGEN are Trademarks of Hormel)
(Samples obtained from Phoenix Chemical Inc.)

Protein Reaction Sequence

All Protein reactants are commercially as indicated above.

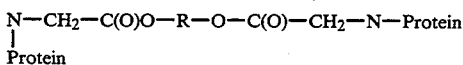

"N-Protein" is the protein or amino acid in which the "N" was the "N" in the amino group.

"R" contains the polyoxyalkylene portion of the molecule.

The following examples further illustrate the objects and advantages of this invention, though it should be understood that the various reactants and amounts thereof, reaction conditions, and other details are merely illustrative and should not be construed to unduly limit this invention.

General Reaction Procedure

The products of the present invention are generally prepared in aqueous solution or dispersion. The preferred concentration is about 50% solids. Additionally, alcohols such as methanol, ethanol, isopropanol, glycols such as ethylene glycol, propylene glycol, polyoxypropylene glycol, polyoxyethylene glycol, hexylene glycol, and cyclomethicone can be added to improve clarity if desired.

To a suitable flask, equipped with a thermometer and agitator is added the specified amount of water. Heat to 50 C. Next add the specified amount of the type of protein reactant and the specified amount of the specified halo ester under good agitation. The reaction mass is heated to 85-95 C. and held from between 5 and 15 hours. The reaction progress is monitored by % inorganic chloride, which approaches 98% of theoretical.

EXAMPLE 89

To a suitable flask, equipped with a thermometer and agitator is added 1,250 grams of protein (Example A) and enough water to make the final concentration of solids 35% by weight is added. Heat to 50 C. Next add 146.0 of Example 46 (the halo intermediate), under good agitation. The reaction mass is heated to 85-95 C. and held from between 5 and 10 hours. The reaction progress is monitored by % inorganic chloride, which approaches 98% of theoretical.

EXAMPLES 90-132

Example 89 is repeated, only this time the specified amount and type of protein and the specified amount of the specified halo intermediate is added.

| | Protein Reactant | | Halo Glycol Reactant | | Water |
|---|---|---|---|---|---|
| Example | Example | Grams* | Example | Grams | Grams |
| 90 | B | 2,500 | 47 | 238.0 | 400.0 |
| 91 | C | 7,500 | 48 | 338.0 | 500.0 |
| 92 | D | 750 | 49 | 488.0 | 700.0 |
| 93 | E | 137,500 | 50 | 538.0 | 700.0 |
| 94 | F | 250 | 51 | 763.0 | 900.0 |
| 95 | G | 1,255 | 52 | 1688.0 | 2000.0 |
| 96 | H | 2,750 | 53 | 2338.0 | 2700.0 |
| 97 | I | 500 | 54 | 4038.0 | 4500.0 |
| 98 | J | 7,900 | 56 | 91.0 | 400.0 |
| 99 | K | 250,000 | 57 | 295.5 | 650.0 |
| 100 | L | 2,800 | 58 | 166.8 | 350.0 |
| 101 | M | 72,500 | 59 | 222.0 | 500.0 |
| 102 | N | 2,560 | 60 | 332.2 | 600.0 |
| 103 | O | 25,210 | 61 | 141.0 | 250.0 |
| 104 | A | 1,205 | 62 | 244.0 | 450.0 |
| 105 | B | 2,500 | 63 | 347.0 | 500.0 |
| 106 | C | 7,500 | 64 | 450.0 | 700.0 |
| 107 | D | 750 | 65 | 288.1 | 500.0 |
| 108 | E | 137,500 | 66 | 177.8 | 350.0 |
| 109 | F | 250 | 67 | 354.4 | 600.0 |
| 110 | G | 1,255 | 68 | 258.6 | 500.0 |
| 111 | H | 2,750 | 69 | 269.8 | 500.0 |
| 112 | I | 500 | 70 | 501.5 | 700.0 |
| 113 | J | 7,900 | 71 | 181.0 | 400.0 |
| 114 | K | 250,000 | 72 | 226.0 | 550.0 |
| 115 | L | 2,800 | 73 | 301.0 | 3500.0 |
| 116 | M | 72,500 | 74 | 90.6 | 300.0 |
| 117 | N | 2,560 | 75 | 295.5 | 500.0 |
| 118 | O | 25,210 | 76 | 166.8 | 750.0 |
| 119 | A | 1,025 | 77 | 244.0 | 1000.0 |
| 120 | B | 2,500 | 78 | 336.0 | 1000.0 |
| 121 | C | 7,500 | 79 | 141.0 | 900.0 |
| 122 | D | 750 | 80 | 214.5 | 350.0 |
| 123 | E | 137,500 | 81 | 347.0 | 500.0 |
| 124 | F | 250 | 82 | 450.0 | 600.0 |
| 125 | G | 1,255 | 83 | 284.5 | 500.0 |
| 126 | H | 2,750 | 84 | 181.5 | 450.0 |
| 127 | I | 500 | 85 | 352.5 | 600.0 |
| 128 | J | 7,900 | 86 | 238.5 | 500.0 |
| 129 | K | 250,000 | 87 | 269.8 | 500.0 |
| 130 | L | 2,800 | 88 | 501.5 | 800.0 |
| 131 | M | 72,500 | 45 | 138.0 | 350.0 |
| 132 | N | 2,560 | 46 | 188.0 | 375.0 |

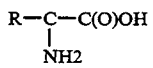

RESULTS

Each of the classes of crosslinked protein products provide unexpected benefits when applied to the hair.

The differing benefits appears to be related to the class of polyoxyalkylene glycol upon which the crosslinked protein are based. A summary is as follows:

Class 1 Polyoxyethylene glycols (ie. b,c, and d are 0.)

Proteins crosslinked with this class of polyoxyalkylene glycol have the highest amount of water absorbed into the shaft of the hair. The molecules prepared using these intermediates have the greatest water solubility, suggesting their usage in shampoo systems as two in one products. These materials are very compatible with anionic systems.

Class 2
Polyoxyethylene/Polyoxypropylene/Polyoxyethylene glycol (ie. a is zero)

Crosslinked proteins based upon his class of materials find usage in conditioner applications and have less compatibility with anionic systems, but surprisingly have a tendency to lower the skin irritation tendencies of traditional cationic surface active agents.

Class 3 Polyoxypropylene Compounds (a, c and d are each 0)

The crosslinked proteins based upon the compounds of this class of compounds have the best liquidity. They surprisingly provide a dramatic reduction in the fiber to metal friction between the hair and a metal comb. This suggests the use of these materials as combability additives to provide both improved provide bet comb and manageability of blow dried hair.

Class 4
Polyoxypropylene/Polyoxyethylene/Polyoxypropylene glycol (ie. d is zero)

The terminal hydroxyl groups are on polyoxypropylene groups, making them secondary. This results in a more steric hindrance and longer reaction times and somewhat lower conversions to the halo ester than those compounds based upon the primary hydroxyl group. The presence of the polyoxypropylene group in the terminal positions of the molecule introduces surprisingly liquidity, hydrophobicity, hydrolytic stability and lubrication properties when compared to the homologs of other groups.

Consequently, based upon unexpected properties, the products based upon group 4 are the most preferred, followed by the products based upon the group 2 glycols.

What is claimed:

1. A crosslinked protein polymer prepared by the reaction of an intermediate conforming to the following structure:

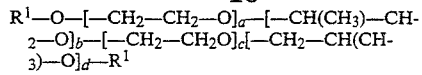

wherein;
R$^1$ is —C(O)—CH$_2$—Cl
a, b c and d are independently integers from 0 to 100, with the proviso that a+b+c+d be greater than 2; with an amino acid source compound selected from the group consisting of a protein or an amino acid, said reaction carried out in aqueous solution at a concentration of between 20 and 80% solids and at a temperature of between 40° and 100° C.

2. A crosslinked protein polymer of claim 1 wherein a is 0.

3. A crosslinked protein polymer of claim 1 wherein b, c, and d are each zero.

4. A crosslinked protein polymer of claim 1 wherein a, c and d are each zero.

5. A crosslinked protein polymer of claim 1 wherein d is 0.

6. A crosslinked protein polymer of claim 1 wherein said protein is a hyrolyzed wheat protein.

7. A crosslinked protein polymer of claim 1 wherein said protein is an oat protein.

8. A crosslinked protein polymer of claim 1 wherein said protein is a soya protein.

9. A crosslinked protein polymer of claim 1 wherein said protein is hydrolyzed collagen.

10. A crosslinked protein polymer of claim 1 wherein said protein is hydrolyzed keratin.

11. A crosslinked protein polymer of claim 1 wherein said protein is placental protein.

12. A process for treating hair which comprises contacting the hair with an effective conditioning amount of a crosslinked protein polymer prepared by the reaction of an intermediate conforming to the following structure:

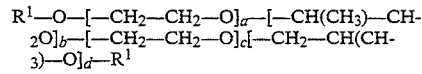

wherein;
R$^1$ is —C(O)—CH$_2$—Cl
a, b c and d are independently integers from 0 to 100, with the proviso that a+b+c+d be greater than 2; with an amino acid source compound selected form the group consisting of a protein or an amino acid, said reaction carried out in aqueous solution at a concentration of between 20 and 80% solids and at a temperature of between 40° and 100° C.

13. A process of claim 12 wherein a is 0.

14. A process of claim 12 wherein b, c, and d are each zero.

15. A process of claim 12 wherein a, c and d are each zero.

16. A process of claim 12 wherein d is 0.

* * * * *